(12) United States Patent
Filipi et al.

(10) Patent No.: US 8,753,306 B2
(45) Date of Patent: Jun. 17, 2014

(54) TISSUE RESECTION DEVICE AND METHOD

(71) Applicant: Creighton University, Omaha, NE (US)

(72) Inventors: Charles J. Filipi, Omaha, NE (US); Timothy B. Hunt, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 13/946,280

(22) Filed: Jul. 19, 2013

(65) Prior Publication Data

US 2014/0031740 A1    Jan. 30, 2014

Related U.S. Application Data

(60) Provisional application No. 61/673,398, filed on Jul. 19, 2012.

(51) Int. Cl.
*A61B 17/20* (2006.01)

(52) U.S. Cl.
USPC ............... 604/22; 604/35; 606/170; 606/159

(58) Field of Classification Search
USPC ............................. 604/22, 35; 606/170, 159
See application file for complete search history.

*Primary Examiner* — Kevin C Sirmons
*Assistant Examiner* — Deanna K Hall
(74) *Attorney, Agent, or Firm* — Woodard, Emhardt, Moriarty, McNett & Henry LLP

(57) ABSTRACT

Among other things, embodiments of devices (and parts thereof) are disclosed that can be used in treating Barrett's esophagus. Embodiments may have a suction cavity or window portion having elongated planar floor and ramped end surfaces with suction holes on one or both end surfaces. Examples include one or more fluid injection needles and parts for controlling fluid injection rate based on the rate of needle withdrawal. Embodiments can include one or more injection needles and receiving holes, with the ability to allow injectate to flow into tissue before withdrawing the needle(s), and/or lockout mechanism to prevent resection of tissue by a cutting mechanism prior to injection of fluid. Methods for treatment are also disclosed, and can include inserting a needle completely through tissue, and injecting fluid into tissue while withdrawing the needle back through the tissue, and/or injecting fluid into tissue while moving the needle forward through tissue.

10 Claims, 12 Drawing Sheets

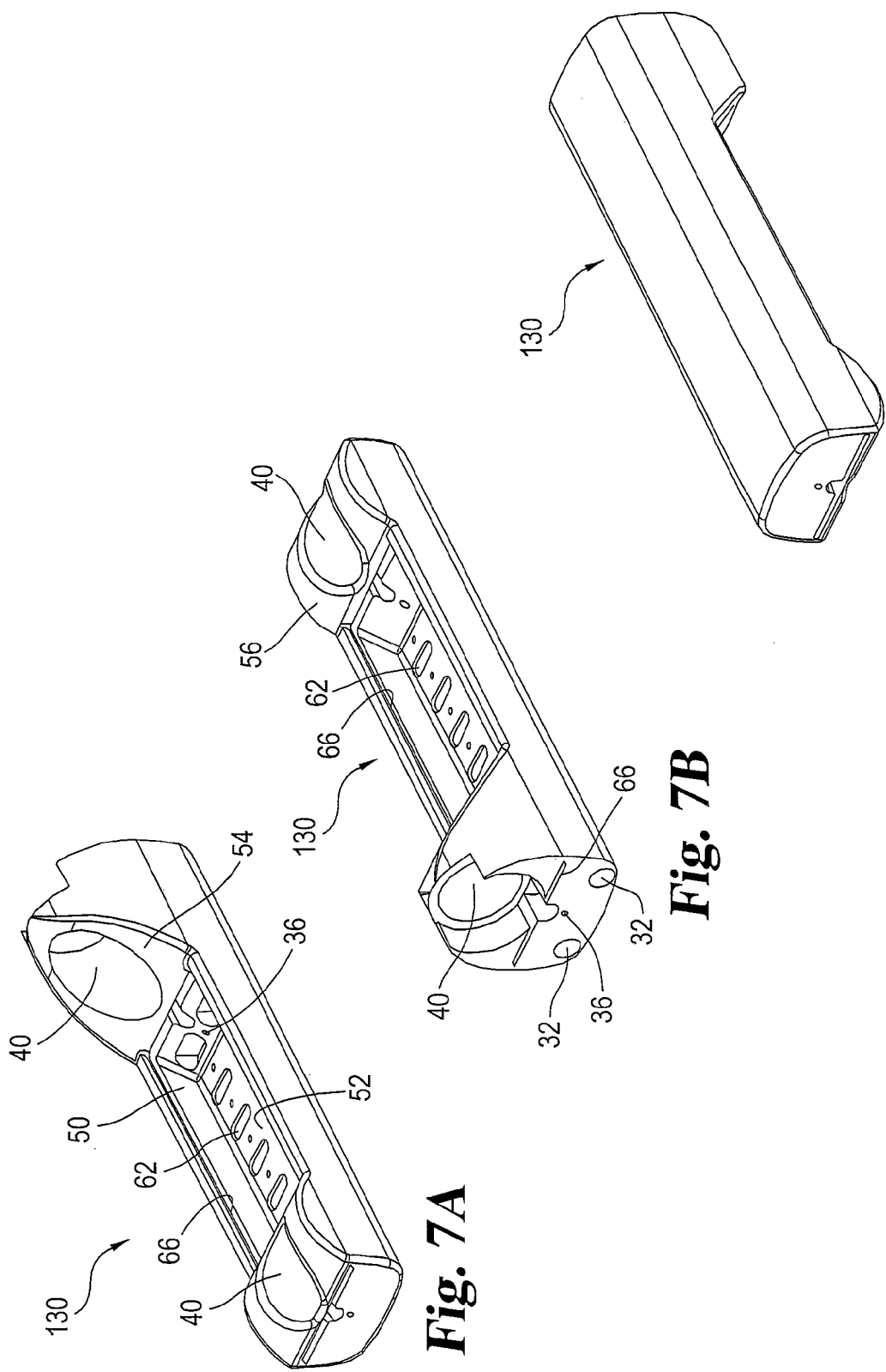

TISSUE RESECTION DEVICE AND METHOD

This application is generally related to the resection of potentially abnormal tissue from inside a patient, wherein the resection may be for therapeutic and/or diagnostic purposes. More particularly, but not exclusively, this application describes systems and techniques for harvesting a thin slice of tissue over a relatively large area in a minimally invasive manner. In a particular embodiment, this application describes a device configured for use in treating Barrett's esophagus.

This application claims the benefit of U.S. Provisional Application Ser. No. 61/673,398, filed on Jul. 19, 2012, and incorporates by reference the same herein in its entirety.

SUMMARY

Among other things, there are disclosed embodiments of tissue resection devices (and parts thereof) usable in treating Barrett's esophagus. Exemplary devices include one or more fluid injection needles and devices for controlling the injection rate based on the rate of needle withdrawal. A positive stop behind the needle plunger may be provided. Device embodiments can include one or more distal injection needles and receiving holes, with the ability to allow injectate to start flowing into the tissue prior to withdrawing the needle(s), and/or lockout mechanism to prevent excision or resection of tissue by a cutting mechanism prior to injection of a fluid into tissue. Embodiments of devices for treating Barrett's esophagus are disclosed with a suction cavity or window portion having elongated planar floor and ramped distal and proximal end surfaces with suction holes on one or both of the ramped end surfaces, and with a low profile section distal to the distal ramp. A small gauge injection needle may be positioned in the suction cavity at about ⅓ the height from the bottom of a cutting mechanism, and/or centered about 1 mm above floor of suction cavity.

Methods for treating Barrett's esophagus are also disclosed. Such methods can include inserting a needle completely through tissue, and injecting fluid into tissue while withdrawing the needle back through the tissue. They can include inserting a needle completely through tissue, and injecting fluid into tissue while moving the needle forward through tissue. Delivery of injectate can be controlled by basing the rate of injection on the rate of needle withdrawal.

These and other embodiments are further described below.

BRIEF DESCRIPTION OF THE DRAWINGS

FIGS. 7A-7D show an alternative embodiment of the portion shown in FIG. 4, which can be used with the embodiment of FIG. 1.

DESCRIPTION OF ILLUSTRATED EMBODIMENTS

Figure 1:
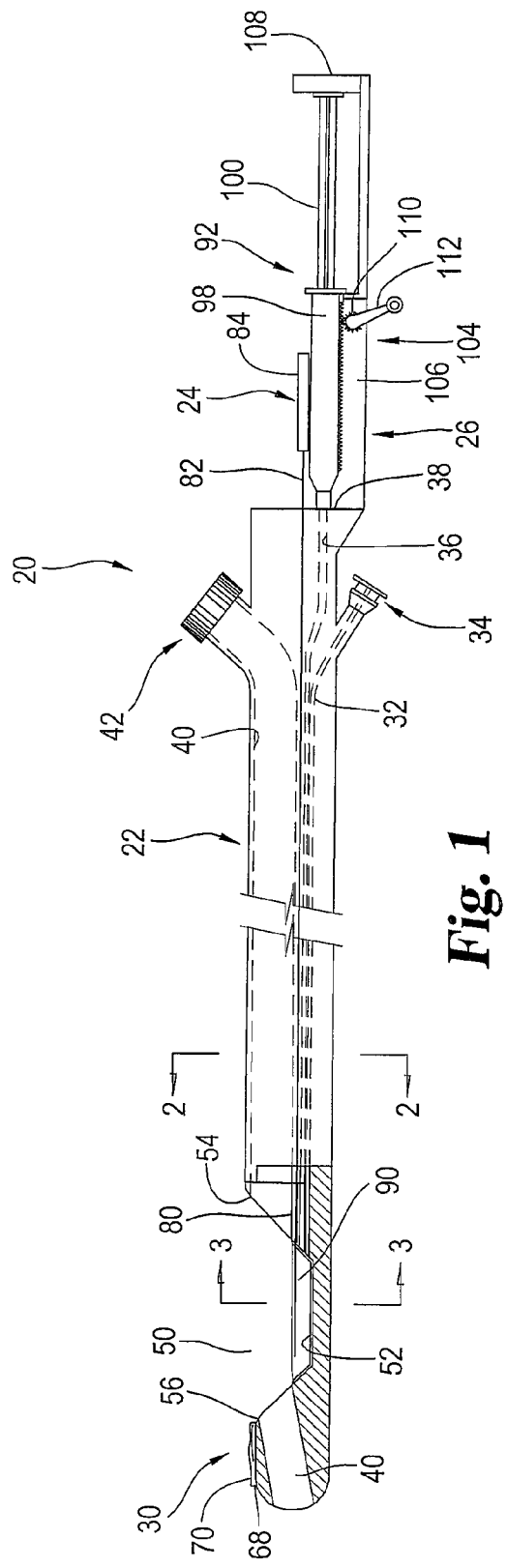
FIG. 1 is side, part cross-sectional view of an embodiment of a device according to the present disclosure.

For the purposes of promoting an understanding of the principles of the disclosure, reference will now be made to the embodiments illustrated in the drawings and specific language will be used to describe the same. It will nevertheless be understood that no limitation of the scope of the claims is hereby intended. Alterations and further modifications in the illustrated devices, and such further applications of the principles of the disclosure as illustrated herein are contemplated as would normally occur to one skilled in the art to which the disclosure relates.

Referring generally to the drawings, there are shown embodiments of a device 20 for excising and removing tissue, which is useful in treatment of Barrett's esophagus. Device 20 in the embodiment of FIG. 1 includes a flexible tube or shaft 22, an excision or cutting mechanism 24, and an injection needle system 26. Each of excision mechanism 24 and needle system 26 are operable from the proximal end of shaft 22, which remains outside the patient, to perform tasks at or near the distal end of shaft 22 which is inside the patient, e.g. at the site of treatment for Barrett's esophagus.

Flexible tube or shaft 22 includes a working end 30 at its distal end, a suction lumen 32 extending from a proximal opening or connection 34 to working end 30, a needle lumen 36 extending from a proximal opening or connection 38 to working end 30, and an endoscope lumen 40 extending from a proximal opening or connection 42 to working end 30. In the illustrated embodiment, needle lumen 36 is substantially between suction lumen 32 and endoscope lumen 40. Further, the illustrated embodiment shows suction lumen 32 along a bottom or underside of shaft 22, i.e. a side that does not intersect or include a portion of the opening in working end 30 (discussed further below), and endoscope lumen 32 along a top or upper side of shaft 22 so that it intersects or passes through that opening. The flexibility of shaft 22 is sufficient for it to move through the esophagus, in one example, to be maneuvered into a position in which working end 30 is adjacent a location for treatment.

Figure 2:
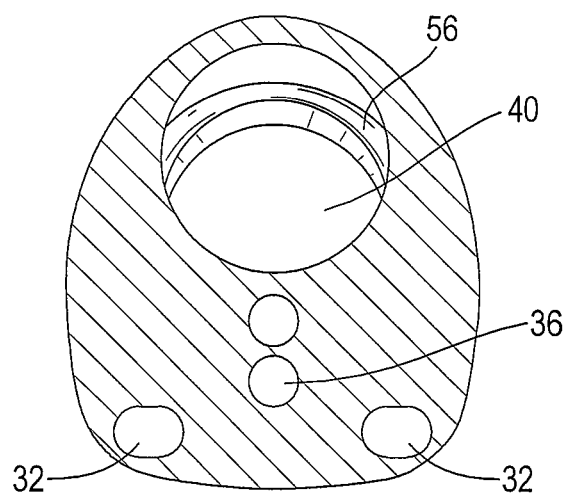
FIG. 2 is a cross-sectional view taken along the lines 2-2 in FIG. 1 and viewed in the direction of the arrows.
Figure 3:
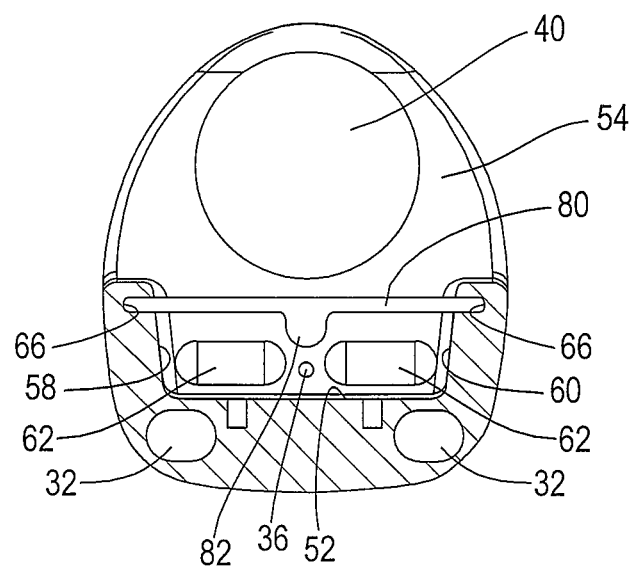
FIG. 3 is a cross-sectional view taken along the lines 3-3 in FIG. 1 and viewed in the direction of the arrows.

Suction lumen 32 in the illustrated embodiment extends outside of shaft 22 at its proximal end, so that connection 34 is exterior of shaft 22. Connection 34 in particular embodiments includes a locking, snap or other secure connection for engaging a suction source (not shown). Suction lumen 32 is substantially linear in this embodiment, which branches at or in working end 30 (see, e.g., FIGS. 2-3) to open into suction apertures, as will be noted further below. Lumen 32 is of a diameter to allow sufficient suction to be applied through it to the working end 30 to permit portions of tissue (e.g. tissue affected by Barrett's esophagus) to be drawn into working end 30 by the suction.

Needle lumen 36 extends from proximal opening 38 substantially linearly to an opening at working end 30, as discussed below. As seen in FIG. 1, in certain embodiments lumen 36 includes a deviation or jog toward its proximal opening 38, to accommodate spacing of injection needle system 26 and excision mechanism 24. Lumen 36 is of a diameter to allow sliding passage of a portion of injection needle system 26, as described below, preferably without significant friction and without significant play between the sliding part of injection needle system 26 and lumen 36.

Endoscope lumen 40 in the illustrated embodiment extends outside of shaft 22 at its proximal end, so that its connection 42 is exterior of shaft 22, for example diametrically opposed to the exterior extension of connection 34 of suction lumen 32. Endoscope lumen 40 is substantially linear in this embodiment, and extends to and through working end 30 in the illustrated embodiment. Lumen 40 is of a diameter to allow sliding passage of an endoscope (not shown), as described below, preferably without significant friction and without significant play between the endoscope and lumen 40.

Working end 30 is shown in FIG. 1 in a particular embodiment that includes a side-directed window or channel 50, having a floor surface 52, oblique proximal and distal surfaces 54, 56, and side surfaces 58, 60. Floor surface 52 is generally planar in the illustrated embodiment and includes a number of suction openings 62, which are connected to suction lumen 32. In particular embodiments floor 52 includes a number of needles or spikes (indicated schematically in FIG. 4 by items 64), which may be static or move up and down with respect to floor 52 through holes. The embodiment shown in FIG. 4 has spikes 64 or their holes evenly spaced with respect to each other and suction openings 62.

Figure 4:
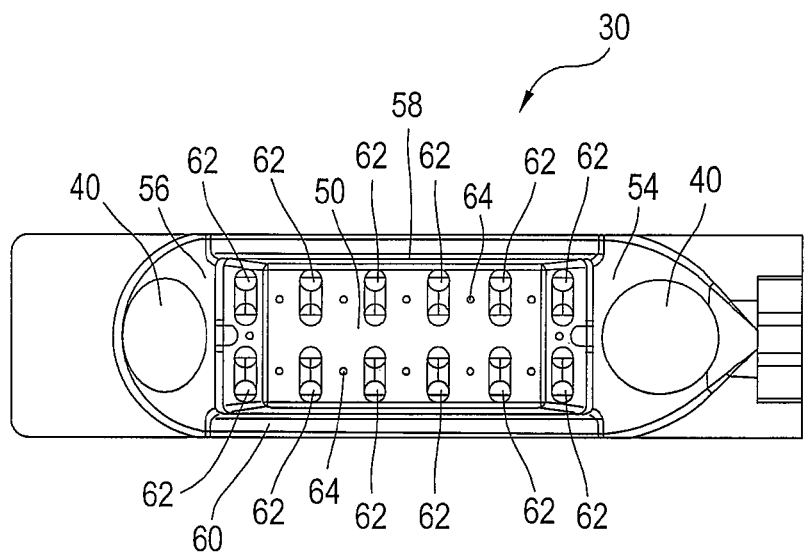
FIG. 4 is a top view of a portion of the embodiment of FIG. 1.

Proximal and distal surfaces 54, 56 are oblique with respect to floor surface 52 and the longitudinal axis of working end 30. In the embodiment of FIGS. 1 and 4, both surfaces 54, 56 are substantially planar. While each surface 54, 56 may define different angles with surface 52, in that embodiment the angle between surfaces 54, 56 and floor 52 are each obtuse, for example of approximately 135 degrees, to allow easy obtaining of tissue into channel 50 and movement of an endoscope through lumen 40. The embodiment of FIG. 4 also shows a portion of surfaces 54, 56 below the uppermost extent of side surfaces 58, 60, and in that portion additional suction openings 62 are found. Endoscope lumen 40 has an opening in each of surfaces 54, 56, so that lumen 40 may be thought of as extending through or over an open portion of channel 50.

Side surfaces 58, 60 in this embodiment are generally planar and parallel to the longitudinal axis of working end 30, meeting floor 52 at a slightly obtuse angle, so that suction through floor 52 is not impeded and is guided to an area somewhat larger than that of floor 52. A longitudinal groove 66 extends along each of side surfaces 58, 60 for guiding the blade of excision mechanism 24.

In particular embodiments, the portion of device 20 or of working end 30 including all or most of window 50 (see, e.g., FIG. 4) is rigidly formed, and may be a rigid capsule or component fixed to flexible portion 22. The distal end of working end 30, e.g. a portion enclosing the distal part of lumen 40 may also be flexible. Thus, in a specifically contemplated embodiment a flexible tube 22 is joined to a rigid capsule (e.g. starting at the right end of FIG. 4 as depicted and extending to a location at or near the enclosure of lumen 40 toward the left end of FIG. 4), and a flexible distal end is joined to the capsule. A rigid suction and cutting area is sandwiched between flexible elements.

In the embodiment in FIG. 1, the distal end of working end 30 has a top surface 68, on which can be placed a coagulation or ablation element 70. In particular embodiments, such a coagulation or ablation element 70 is an energized element, for example using electrical, heat or other energy to promote coagulation or to cauterize an excision area, or to remove further material from the excision area. The FIG. 1 embodiment shows the portion of endoscope lumen 40 that extends through the distal end of working end 30, e.g. under element 70, as being non-parallel to the longitudinal axis of working end 30. In that embodiment lumen 40 is substantially linear and points toward the longitudinal axis as it goes from channel 50 to the distal tip of working end 30. In other embodiments, the portion of lumen 40 in the distal tip can have a curve, such as a curve generally concave as it faces window 50.

Excision or cutting mechanism 22 in the embodiment of FIG. 1 includes a cutting blade 80, a handle, grip or other control 82, and a force transmitting portion 84. Blade 80 is a thin flat member with a forward sharp edge, and has a width sufficient to slide within groove 66 in channel 50. In particular embodiments, blade 80 is of a metal substance, such as stainless steel. Force transmitting portion 84 in this embodiment is a semi-rigid rod or shaft, flexible enough to accommodate flexing of shaft 22 during use of device 20, and rigid enough to force blade 80 forward through channel 50 and to pull it backward when retraction is desired. Portion 84 may be a thin metal wire or rod in particular embodiments, and it extends through a passage in shaft 22 (e.g. one dedicated to portion 84, or one that is a part of or connected to needle lumen 36; see FIG. 2). Handle or control 82, which is outside of shaft 22 and the patient, is operable by the user so as to move blade 80 forward and backward through channel 50. In the illustrated embodiment, moving handle 80 forward moves blade 80 along groove 66 distally (i.e. toward surface 56 and away from surface 54), and pulling handle 80 backward moves blade 80 along groove 66 proximally (i.e. away from surface 56 and toward surface 54).

Figure 5:
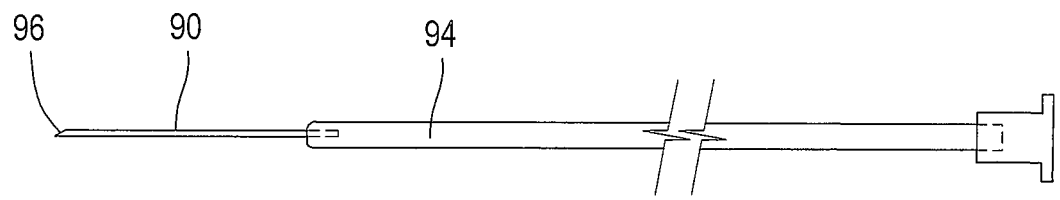
FIG. 5 is a side view of a portion of the embodiment of FIG. 1.
Figure 6:
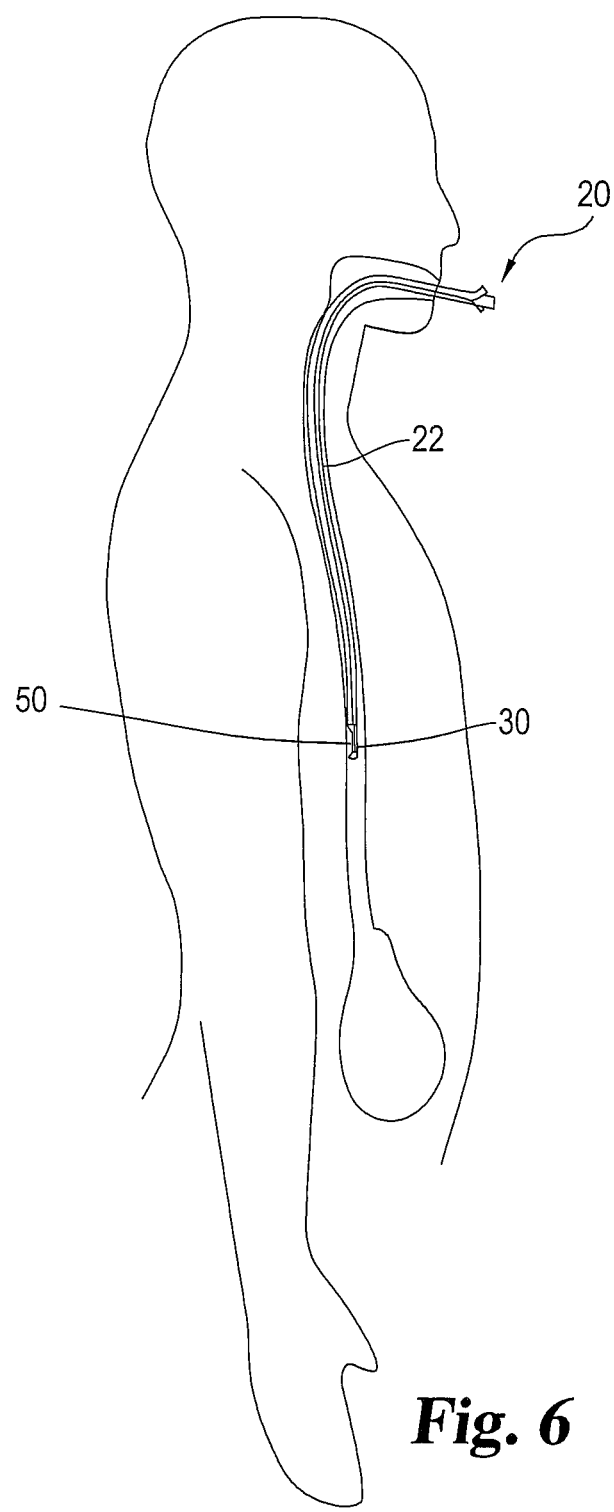
FIG. 6 indicates a transoral application of the embodiment of FIG. 1.
Figure 7D:
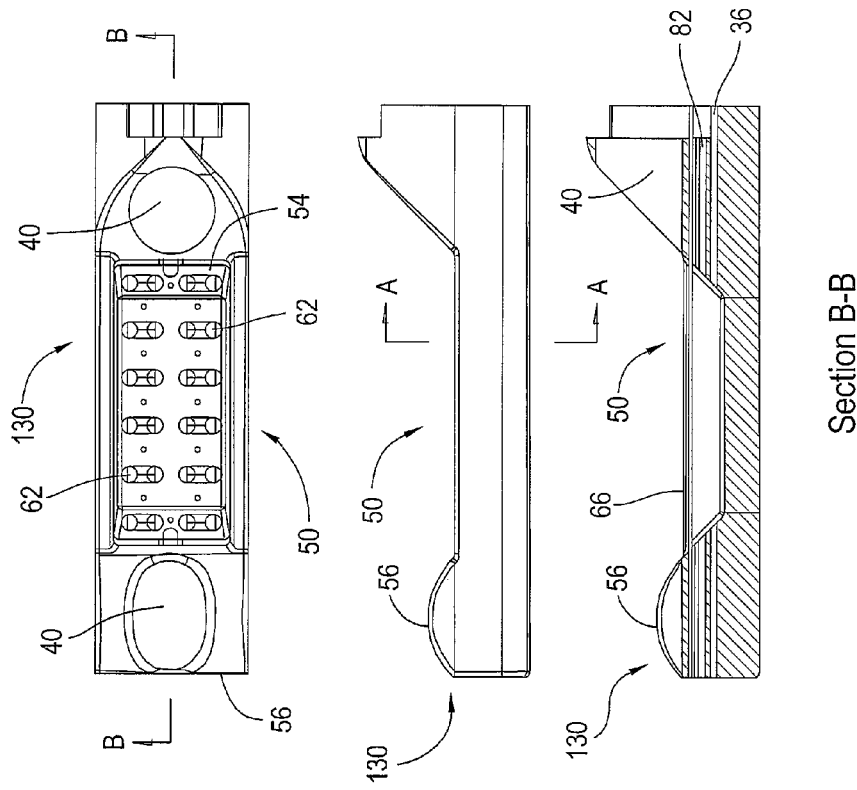
Figure 7D:
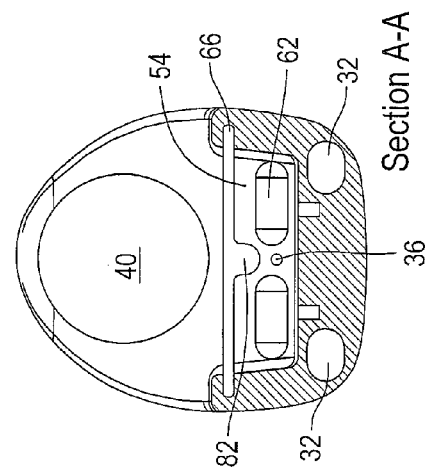
Figure 8:
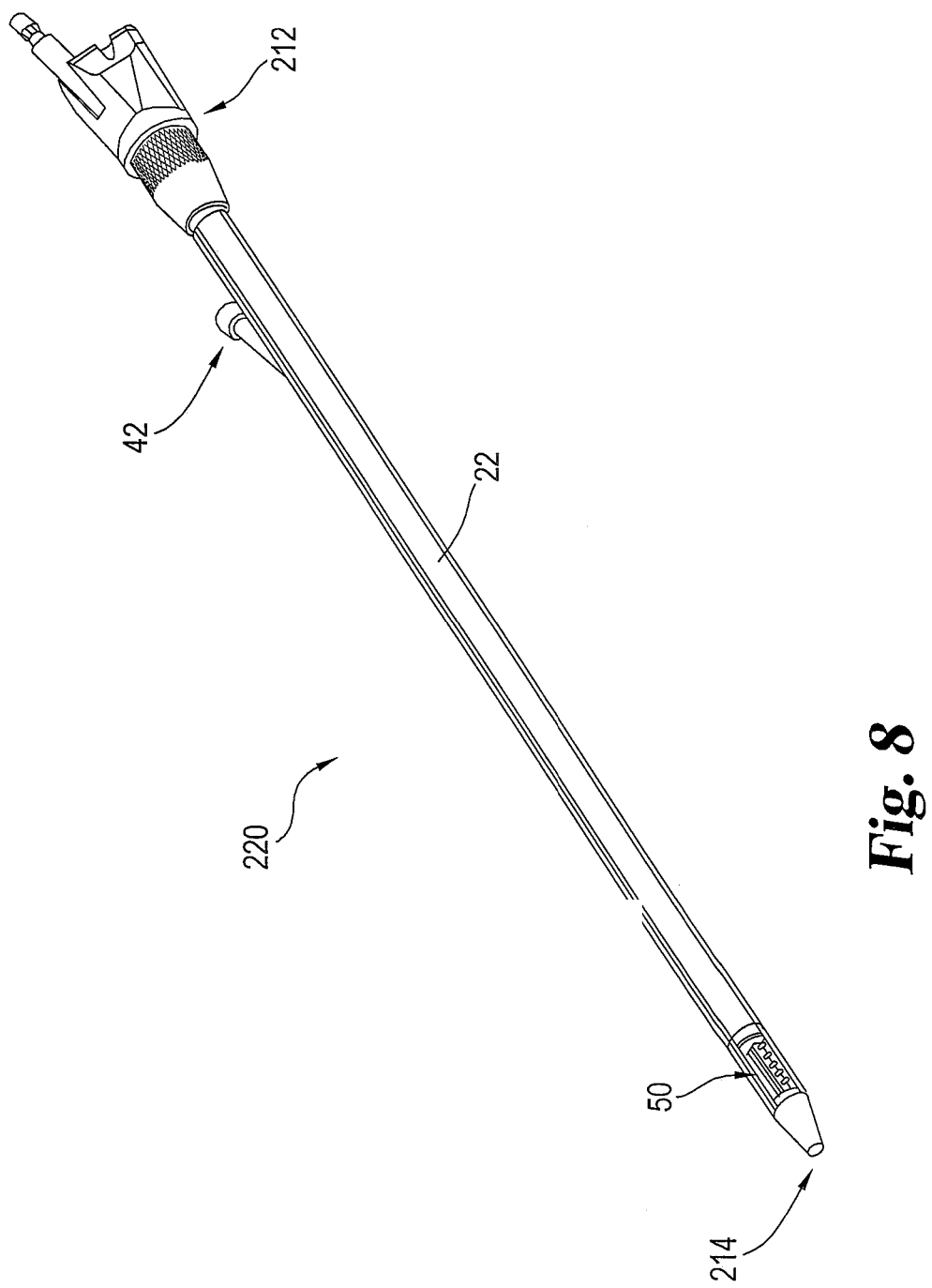
FIG. 8 is a perspective view of an embodiment of a device according to the present disclosure.

Needle system 26 in the embodiment of FIG. 1 includes a distal needle tip 90, a syringe 92, and a conduit 94 connecting syringe 92 and tip 90. Tip 90, in the embodiment of FIG. 5, is a substantially rigid, preferably metal hollow tube with a sharp, open distal end 96. A particular embodiment of tip 90 is of about 27 gauge and is of about 4.5 cm in length, from conduit 94 to end 96. Conduit 94 is a flexible tube fixed to tip 90, e.g. by tip 90 being inserted into and glued or otherwise secured to conduit 94. Conduit 94 may be of any of a number of suitable plastic or other materials that provide flexibility yet also transmit pushing force to tip 90. Since conduit 94 is larger in diameter than tip 90, part of the needle lumen 36 accommodating conduit 94 (see FIG. 2) is larger in particular embodiments than a part of needle lumen 36 accommodating only tip 90 (see FIG. 3). Syringe 92, in the illustrated embodiment, has a barrel 98 and a plunger 100 snugly fitted into barrel 98. Barrel 98 includes a toothed rack 102 longitudinally along its outside surface. Syringe 92, conduit 94 and tip 90 are movable with respect to shaft 22, so that movement of syringe 92 (particularly barrel 98) forward or distally pushes tip 90 via conduit 94 into and through channel 50. In one example, tip 90 can be moved through channel 50 to the extent that part or all of sharp distal end 96 enters a small-diameter portion of needle lumen 36 through surface 56. Conversely, moving barrel 98 of syringe 92 backward (proximally) retracts tip 90 from channel 50 and into shaft 22.

A frame 104 for syringe 92 may be considered a part of needle or injection system 24 or a part of shaft 22. Frame 104 in one embodiment includes a longitudinal arm or cradle 106, an end boss 108, and a gear 110 operable by a handle 112. Syringe 92 sits in or is affirmatively held by arm 106, with rack 102 engaged with gear 110. Handle 112 can thus be used to move barrel 98 (and tip 90) with respect to shaft 22. As will be discussed further below, rotating handle 112 (e.g. counter-clockwise as seen in FIG. 1) moves tip 90 into and through channel 50. Once tip 90 is so extended, barrel 98 can be filled with fluid (e.g. water, saline or other liquid for mucosal lifting) and plunger 100 can be extended (if necessary) so that it abuts boss 108. Turning handle 112 to move barrel 98 and tip 90 proximally (e.g. clockwise as seen in FIG. 1) also forces barrel 98 along plunger 100. Thus, with the single action of turning handle 112, needle tip 90 is retracted through channel 50 and fluid is forced from barrel 98 and through conduit 94 and tip 90. With fluid exiting tip 90 as it is retracted, dispersion of the fluid through the length of tissue within channel 50 is accomplished.

Embodiments having a lock-out mechanism to prevent actuation of the excision mechanism 24 (to move blade 80 forward) without injection of fluid by injection system 26 are also contemplated. FIG. 1 is a representation of a device 20 in which no injection has yet taken place. A lock-out mechanism may be connected between barrel 98 or another part of injection system 26 and handle 84 of the excision mechanism, for example, such that handle 84 cannot be pushed forward until barrel 98 has been moved sufficiently or completely rearward, indicating sufficient or full injection of the fluid.

Exemplary injection systems may achieve one or more of several objectives, such as controlling the injection rate of fluid into captured tissue and/or controlling needle retraction or retraction rate during injection. Control of retraction is shown as mechanical in the above embodiment, but it will be seen that electrical control may be applied to retraction and/or to injection. Such systems may be placed at or near an end of device 20 that is external of the patient, and a lock-out mechanism may prevent excision of tissue prior to injection (or full injection) of fluid into tissue.

Other embodiments of devices for mucosal excision for the treatment of Barrett's esophagus are contemplated. As with the above embodiments, use via endoluminal transoral flexible endoscopic techniques is contemplated.

For example, an embodiment substantially as described above with respect to device 20 and working end 30 includes multiple needles or spikes 64 that are generally oriented toward the proximal end of device 20. That is, from their location on floor 52, such needles 64 are oriented such that their free tips are closer to the proximal end of device 20 than are their respective locations on floor 52. Needles 64 retain tissue within window 50 during cutting by blade 80. Particular embodiments may also include either a single longitudinal needle 90 or multiple such needles laterally spaced from each other (and in specific examples parallel to the path of blade 80 and/or in a plane parallel to the path of blade 80) for injecting fluid into tissue within window 50.

As with the above-described embodiment of working end 30, an endoscope is used (via lumen 40) for visualization and as a guide for insertion of device 20, and as indicated is within or internal of the outer extend of at least portion 22 of device 20. Since the endoscope passes through window 50 of device 20, the endoscope can be used to remove excised tissue within window 50, thereby making it unnecessary to remove device 20 from the patient (with associated discomfort or irritation) in order to remove the excised tissue from the body. Further, a handle mechanism as described dispenses a fixed volume of fluid through the injection needle(s) 90 as the needle(s) are retracted through the tissue, providing even disbursement of fluid through the tissue. A handle mechanism including a knob or actuator attached to both the mover of needle(s) 90 and to the syringe plunger 100 can disburse fluid through the needles as the needles are being inserted, again providing even application of fluid through the tissue.

Figure 14:
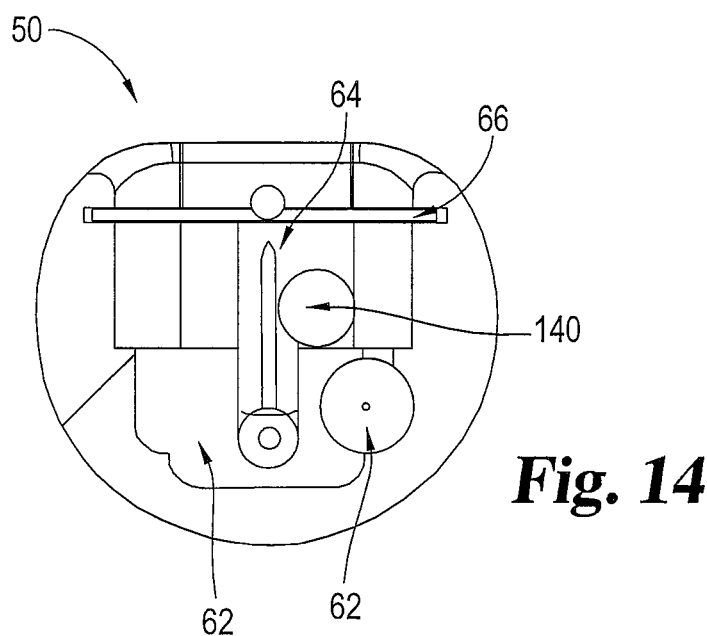
FIG. 14 is a cross-sectional view of the embodiment of FIG. 13.
Figure 15:
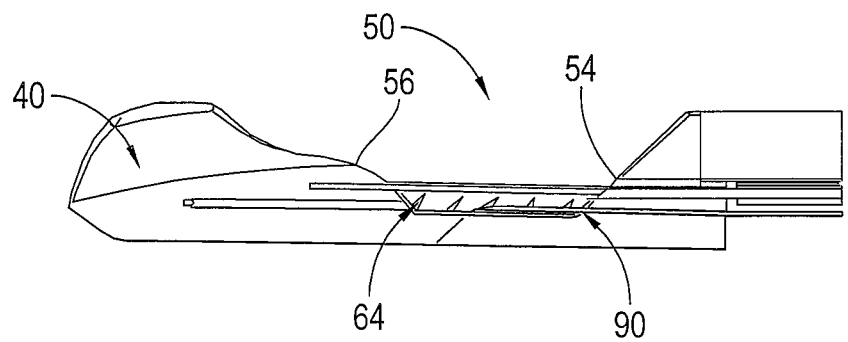
FIG. 15 is a side part cross-sectional view of an embodiment of a portion of a device according to the present disclosure, which may be used with other structures described herein.

Other embodiments are also contemplated with one or more fixed radial injection needles 64. The height of needles 64 relative to the location of blade 80 and the depth of window 50 is determined so that as suction is provided through cavities 62 the needles 64 penetrate to a desired depth in the tissue, and provide a desired cut depth. Such an embodiment may an internal lumen sized for a guide wire (e.g. similar to but smaller than lumen 40 discussed previously, see 140 in FIG. 14), and an endoscope may be used for visualization outside the device. Suction cavities 62 on either side of the radial needles 64 provide force on tissue on either side of the needles, providing even penetration of the needles into the tissue. As with prior embodiments, fluid is delivered to the injection needles 64 via a syringe in this example.

As further examples, FIGS. 7A-D show an embodiment of a working end 130. Working end 130 is quite similar to working end 30 described above, with similar or identical elements labeled as described above. While the distal end of working end 30 (FIG. 1) is closed over lumen 40, in this embodiment the distal end is open, so that lumen 40 is open. Surface 56 in this embodiment is rounded, e.g. cylindrical around an axis substantially perpendicular to the longitudinal axis of working end 130. In this embodiment, a separate piece may be attached to the distal end to enclose and/or extend lumen 40, and such a separate piece may include a coagulation or ablation element 70 as noted above. It will be understood that embodiments of working end 30 and 130 may be fashioned as part of shaft 22, or may be separately constructed and fixed to shaft 22. In this or other embodiments, working end 130 can be rigid, with shaft 22 being flexible and any separate piece at the distal end of working end 130 being flexible, for comfort and ease in insertion of device 20 into the patient.

An example of use in treating Barrett's esophagus is discussed below. It will be understood that other uses of device 20 may be made. Device 20 is inserted transorally through the esophagus to a position in which channel 50 generally faces a portion of esophageal tissue (e.g. projecting red mucosa) to be excised. As one example, an endoscope (not shown) extending through endoscope lumen 40 and beyond the distal tip of device 20 may be used to find and view the tissue of interest. With the endoscope oriented toward the tissue of interest, device 20 is moved along the endoscope to the desired location and position. The endoscope can be used to verify that channel 50 is facing the tissue of interest, and is withdrawn at least from channel 50. The endoscope may remain in lumen 40 proximal of channel 50 so as to visualize use of device 20.

Suction is applied through suction channel 32 and suction openings 62 to draw the tissue of interest into channel 50. With the mucosa of the tissue within channel 50, i.e. between side surfaces 58, 60 and proximate or against floor 52, needle tip 90 is advanced through the mucosa as indicated above. With needle tip 90 through the mucosa, and fluid within syringe 92, retraction of needle tip 90 via turning of handle 112 as discussed previously results in fluid delivery along the track of retraction through tissue of tip 90. Delivery of the fluid results in mucosal lifting. With the fluid delivered, and any lock-out mechanism disabled or obviated, handle 84 of excision mechanism is pushed forward, moving blade 80 through the tissue in channel 50 to surface 56. The excised tissue remains in channel 50 due to suction through apertures 62. Blade 80 is retracted by pulling back on handle 84, and the endoscope in lumen 40 may be moved forward to obtain and remove the tissue from channel 50. Also, the endoscope may be used to inspect the excision site and/or to maneuver device 20 to a new excision site. Alternatively, device 20 may be removed from the patient and the tissue then removed from channel 50 manually. In embodiments having a coagulation or ablation element, following excision device 20 may be oriented so that the coagulation or ablation element faces or contacts the location from which tissue was excised. The element is activated to limit or stop bleeding, ablate further cells or tissue, or the like.

FIGS. 8-12 show an embodiment of a device 220 similar in many respects to device 20, and also for excising tissue in treatment for conditions such as Barrett's esophagus. Features shown in those drawings have clear similarities or identity with embodiments discussed above. It is noted that these figures show endoscope and needle lumens that are laterally positioned with respect to each other, and that the endoscope is lower (closer to the floor surface) than the excision blade. An electrocoagulation electrode is shown wrapping around the working end, including a portion to the side (lateral) of the tissue channel or window and a portion under or opposite the channel, and along a longer length than the channel.

Features substantially or entirely identical to those in device 20 are indicated by the same numbers with respect to device 220. As discussed above, device 220 includes a shaft 22, which is connected to a handle 212. An endoscope entry and seal 42, window portion 50 and distal end portion 214 are particularly numbered in FIG. 8. In this embodiment, shaft 22 is flexible as is portion 214, while window portion 50 is in the form of a rigid capsule or component.

Figure 9:
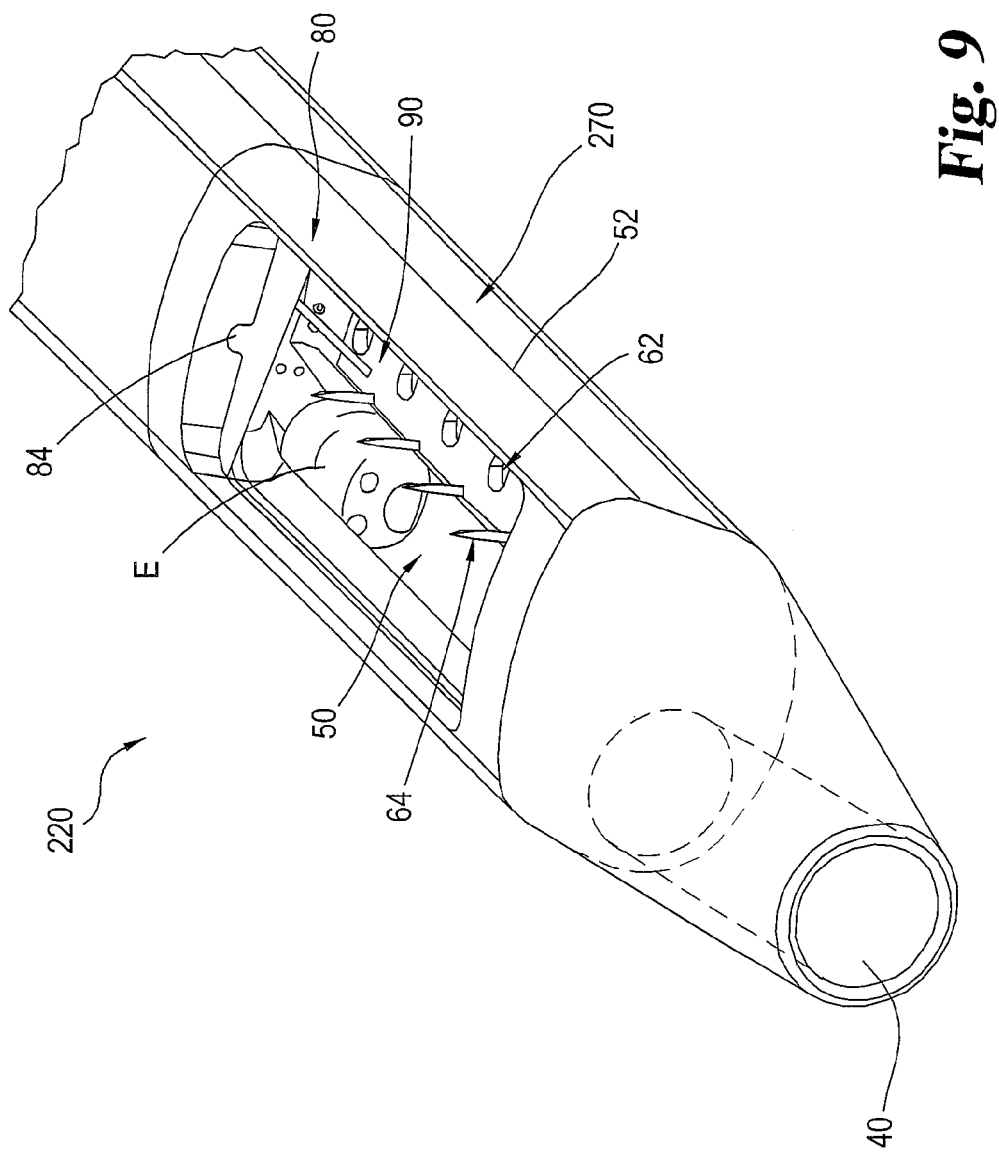
FIG. 9 is a perspective view of a portion of an embodiment as in FIG. 8.

FIG. 9 is a closer view of the working end of device 220, with window portion 50, needles or spikes 64, endoscope lumen 40, suction openings 62, cutting blade 80, force transmitting member 84 and needle tip 90 as discussed above particularly identified. An endoscope E is indicated in lumen 40. It will be seen in this embodiment that at least a portion of lumen 40 and endoscope E are each below the level of cutting blade 80—that is, at least a portion of lumen 40 (and endoscope E within it) are between the cutting blade 80 and the level of floor surface 52. Lumen 40 is also shown lateral of or to one side of floor surface 52 in this embodiment. Spikes 64 may be radial (i.e. central and pointing to or through the center of window portion 50) or may be backward-facing (i.e. pointing generally back to the proximal portion of device 220).

Figure 10:
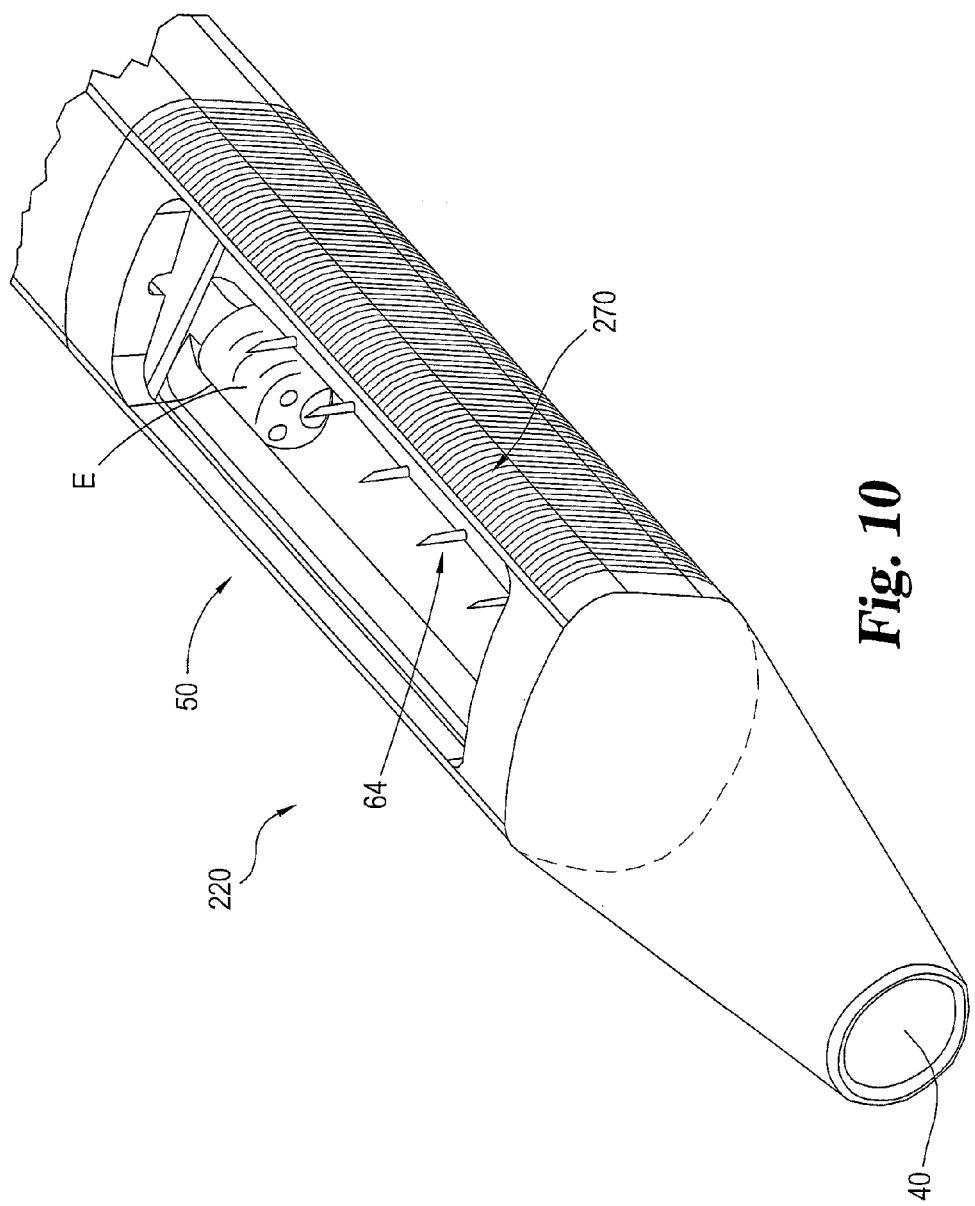
FIG. 10 is a perspective view of a portion of an embodiment as in FIG. 8.
Figure 11:
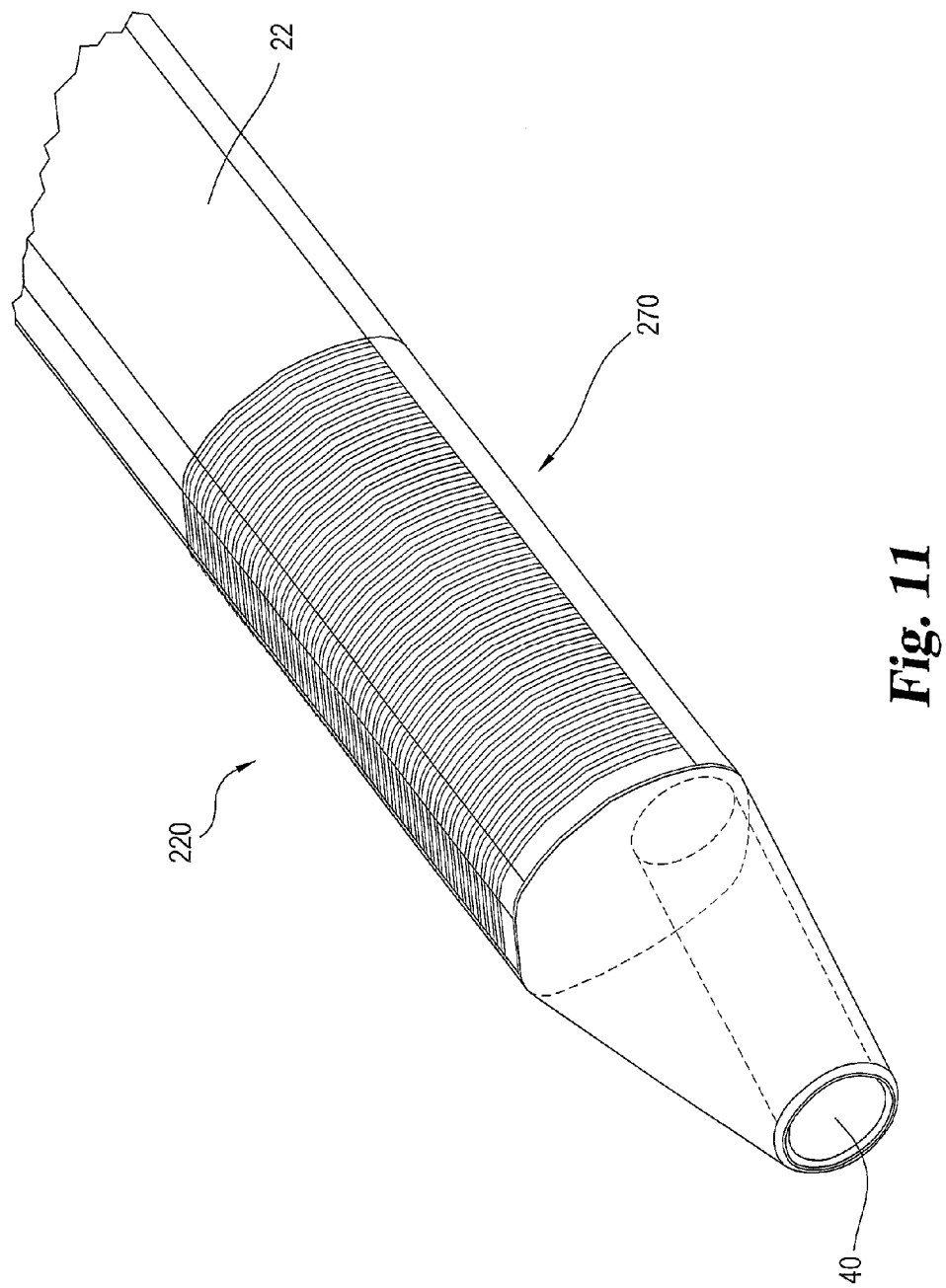
FIG. 11 is a perspective view of an underside of a portion of an embodiment as in FIG. 8.

An area for a coagulation or ablation element 270 is also shown in FIG. 9, and is further indicated in FIGS. 10-11. Element 270, as indicated previously, is an electrical element in particular embodiments for promoting healing after resection of tissue. The illustrated embodiment shows element 270 along a side of device 220 and wrapping around a bottom surface. That arrangement provides for ease of use of element 270 without requiring significant re-orientation of device 220. Further, element 220 is shown along a length greater than that of window portion 50. That is, the ends of element 200 each extend beyond the ends of window portion 50, as a way to make treatment of the full resected length easier.

Figure 12:
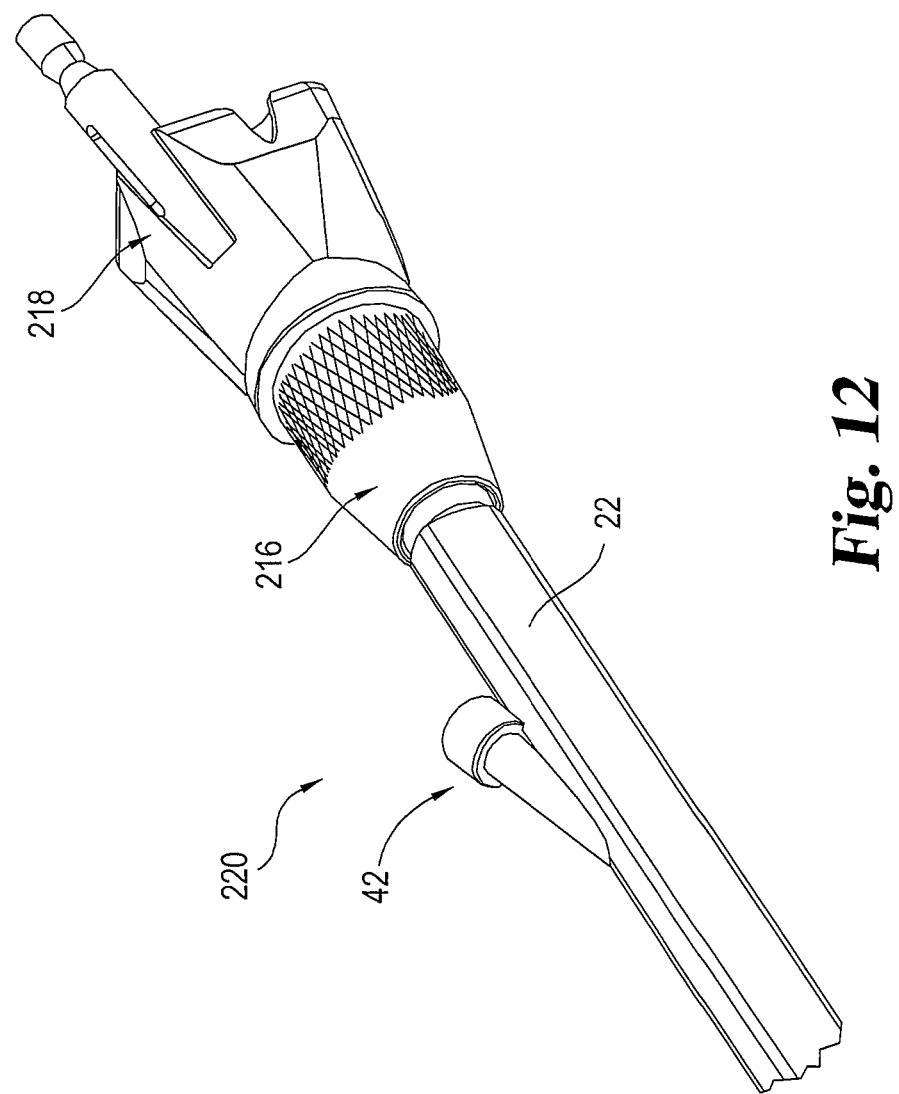
FIG. 12 is a perspective view of a portion of an embodiment as in FIG. 8.
Figure 13:
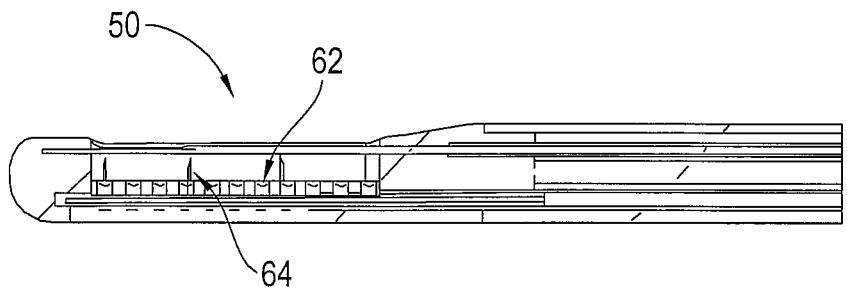
FIG. 13 is a side part cross-sectional view of an embodiment of a portion of a device according to the present disclosure, which may be used with other structures described herein.

FIG. 12 depicts an embodiment of a proximal end of device 220. Particularly shown are endoscope entry and seal 42, a coupling 216 to ensure continuity of the conduits discussed previously between shaft 22 and a removable handle 218.

The embodiments provide not only controlled injection rate of the fluid, but also controlled needle retraction through tissue during the injection. The injection system is a part of or attached to the end of the excision device, for ease of use and handling. The lock-out mechanism, in embodiments in which it is provided, ensures that tissue is not excised before it is ready (i.e. through injection of fluid for mucosal lifting). While the actuation of excision mechanism 24 and injection system 26 is shown and discussed in terms of manual, mechanical operation, it will be understood that electronic controls may be incorporated to govern their use.

Further features and embodiments are contemplated, such as a fluid injection system with a "needle and fluid actuator" fixed to the plunger of a syringe. Pushing the actuator puts pressure on the fluid within the barrel. That pressure pushes fluid out of the barrel, and also applies force to the barrel to move it forward, pushing the needle connected to the barrel into and through tissue. Forward movement of a needle with dispensing of fluid as it travels is accomplished.

While the embodiments have been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the claim scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this disclosure to the specifics thereof. It will be understood that specific structure, features or steps noted with respect to one embodiment or item may be used with or incorporated into other embodiments or items.

In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A device for treating Barrett's esophagus, comprising:
a shaft having a working end with a window portion for accepting mucosal tissue of a patient's esophagus, a suction lumen extending from a first proximal opening to the working end, and a guiding lumen extending from a second proximal opening to the working end, wherein the window portion includes a floor surface, oblique proximal and distal surfaces and side surfaces, a plurality of needles extending from or through the floor surface and a plurality of suction openings through the floor surface and connected to the suction lumen;
a cutting mechanism passing through the shaft, the cutting mechanism including a cutting blade, a handle and a force transmitting portion, the force transmitting portion being movable through the shaft by operation of the handle, the cutting blade being movable through the window portion;

a fluid injection system including a distal needle tip, a syringe, and a conduit connecting the syringe and the needle tip, wherein the syringe includes a barrel and plunger fitted into the barrel, wherein the syringe, conduit and needle tip are movable with respect to the shaft, so that movement of the syringe barrel distally pushes the needle tip along the shaft and through the window portion.

2. The device of claim 1, wherein the working end has a surface on which a coagulation or ablation element is fixed.

3. The device of claim 1, wherein the guiding lumen is sized and configured for an endoscope, and wherein the guiding lumen extends through the window portion so that an endoscope may pass through the window portion between the cutting blade and the floor surface of the window portion.

4. The device of claim 1, wherein the guiding lumen is sized and configured for a guide wire, and wherein the guiding lumen extends through the window portion so that an endoscope may pass through the window portion between the cutting blade and the floor surface of the window portion.

5. The device of claim 1, wherein the needles are evenly spaced with respect to each other and the suction openings.

6. The device of claim 1, wherein the barrel includes a toothed rack, and further comprising a frame for the syringe including a gear operably engaged with the rack, wherein operation of the gear moves the syringe and the needle tip with respect to the shaft.

7. The device of claim 6, wherein the frame includes an end boss, wherein the plunger can abut the end boss and in such condition, operation of the gear simultaneously retracts the needle tip with respect to the shaft and moves the barrel with respect to the plunger to force fluid from the barrel through the conduit and needle tip.

8. The device of claim 1, further including a handle linking the plunger and the needle tip, whereby the plunger and the needle tip can be advanced together.

9. The device of claim 1, wherein the shaft includes a flexible proximal portion joined to a rigid capsule that includes the window portion.

10. The device of claim 1, including a distal end that is flexible attached to the rigid capsule, so that the capsule is sandwiched between the flexible proximal portion and the flexible distal end, the flexible distal end including an enclosed portion of the guiding lumen having a proximal opening facing the window portion and a distal opening.

* * * * *